(12) United States Patent
Dillinger et al.

(10) Patent No.: US 10,226,169 B2
(45) Date of Patent: Mar. 12, 2019

(54) MEDICAL ENDOSCOPE WITH A COOLING DEVICE FOR MOUNTED ELECTRIC COMPONENTS

(75) Inventors: Anja Katrin Dillinger, Aindling (DE); Guenter Wilhelm Schuetz, Augsburg (DE); Christoph Schnuerer-Patschan, Wartenberg (DE)

(73) Assignee: INVENDO MEDICAL GMBH, Kissing (DE)

( * ) Notice: Subject to any disclaimer, the term of this patent is extended or adjusted under 35 U.S.C. 154(b) by 457 days.

(21) Appl. No.: 13/472,994

(22) Filed: May 16, 2012

(65) Prior Publication Data

US 2013/0131451 A1 May 23, 2013

(30) Foreign Application Priority Data

Nov. 18, 2011 (DE) .................... 10 2011 055 526

(51) Int. Cl.
| | | |
|---|---|---|
| *A61B 1/12* | (2006.01) | |
| *A61B 1/04* | (2006.01) | |
| *A61B 1/06* | (2006.01) | |
| *A61B 1/00* | (2006.01) | |
| *A61B 1/05* | (2006.01) | |

(52) U.S. Cl.
CPC .......... *A61B 1/0676* (2013.01); *A61B 1/0011* (2013.01); *A61B 1/128* (2013.01); *A61B 1/05* (2013.01)

(58) Field of Classification Search
USPC ............... 600/136, 141, 160, 174, 176, 127
See application file for complete search history.

(56) References Cited

U.S. PATENT DOCUMENTS

| | | | |
|---|---|---|---|
| 7,371,209 B2 | 5/2008 | Viebach | |
| 7,413,543 B2 | 8/2008 | Banik | |
| 7,914,448 B2 * | 3/2011 | Bob et al. ..................... | 600/175 |
| 8,427,766 B2 | 4/2013 | Ning | |
| 2006/0259024 A1 * | 11/2006 | Turovskiy .............. | A61B 18/18 606/33 |
| 2007/0015962 A1 | 1/2007 | Bob et al. | |
| 2007/0073109 A1 * | 3/2007 | Irion .................... | A61B 1/0051 600/179 |
| 2007/0249907 A1 * | 10/2007 | Boulais et al. ............... | 600/179 |

(Continued)

FOREIGN PATENT DOCUMENTS

JP          4786790          6/2002

*Primary Examiner* — John P Leubecker
*Assistant Examiner* — William Chou
(74) *Attorney, Agent, or Firm* — Standley Law Group LLP

(57) ABSTRACT

An endoscope with a flexible endoscope shaft has an endoscope head arranged at its distal end. The endoscope head is a sleeve, open at both end faces. Functional units, such as an optical system, a working channel, an illumination and a cooling system for the illumination are accommodated in the endoscope head. The cooling system has a heat exchanger integrally formed with the sleeve in the latter which forms a closed cooling chamber for generating a coolant flow. The illumination, which is in the form of an external conductor plate supporting an illumination means, is arranged adjacent to the distal end wall of the heat exchanger, to discharge thermal energy via the end wall of the heat exchanger to the coolant flow. The external conductor plate is mechanically supported on, or has only a minimum distance from, the heat exchanger end wall.

14 Claims, 1 Drawing Sheet

(56) References Cited

U.S. PATENT DOCUMENTS

| | | | |
|---|---|---|---|
| 2007/0260252 A1* | 11/2007 | Schmitz | A61B 17/1659 606/79 |
| 2008/0161748 A1* | 7/2008 | Tolkoff | A61N 5/0603 604/21 |
| 2010/0261969 A1 | 10/2010 | Fischvogt et al. | |
| 2011/0092772 A1* | 4/2011 | Weber | A61B 1/0008 600/178 |
| 2014/0074080 A1* | 3/2014 | Halaka | A61B 18/203 606/16 |
| 2015/0085084 A1* | 3/2015 | Heni | A61B 1/00064 348/50 |

* cited by examiner

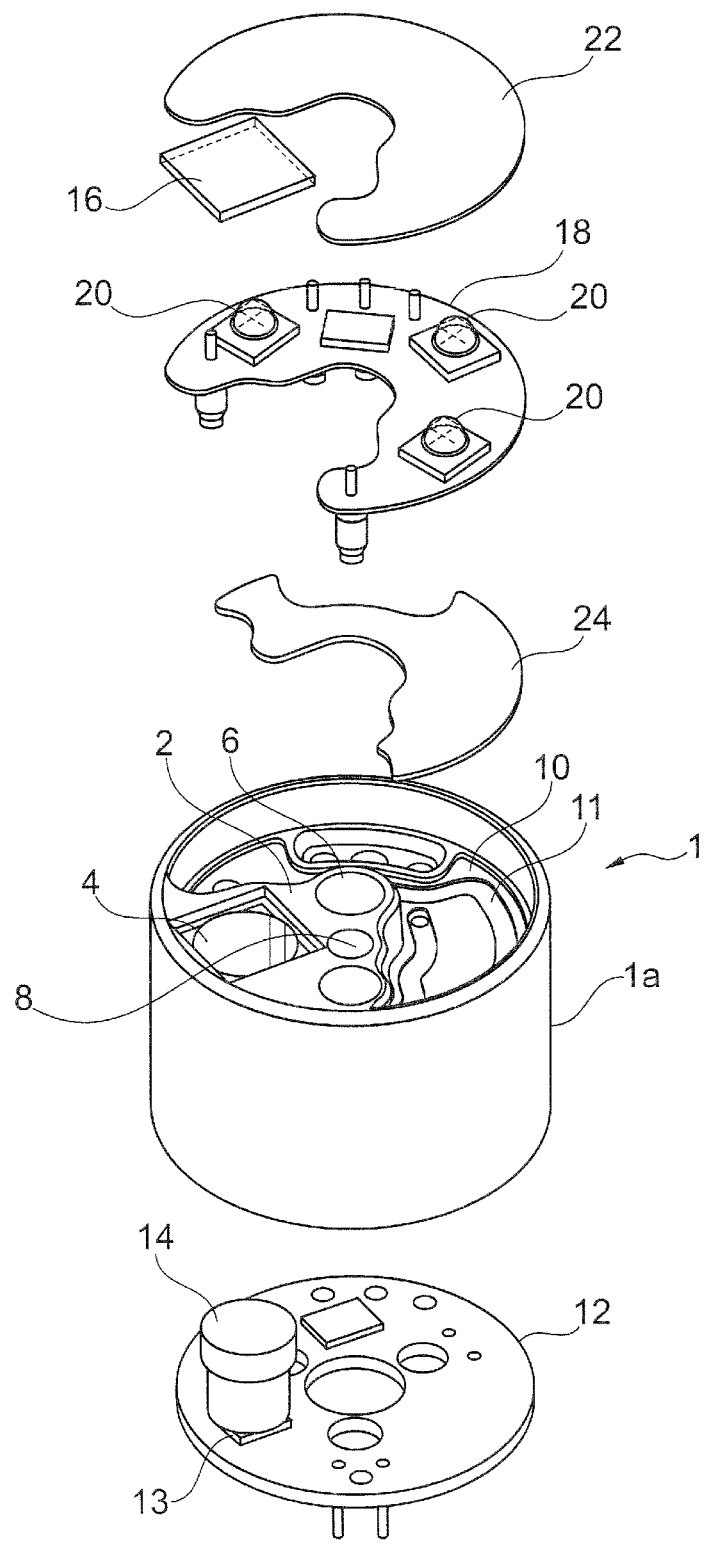

MEDICAL ENDOSCOPE WITH A COOLING DEVICE FOR MOUNTED ELECTRIC COMPONENTS

CROSS-REFERENCE TO RELATED APPLICATIONS

This application is entitled to benefit of a right of priority under 35 USC § 119 from German patent application DE 10 2011 055 526.9, which was filed on 18 Nov. 2011, the content of which is incorporated by reference as if fully recited herein.

TECHNICAL FIELD

The present invention relates to a medical endoscope having electric components being mounted in the endoscope head thereof that are cooled by means of an internal cooling device, and in particular to an endoscope in accordance with the preamble of claim 1.

BACKGROUND OF THE ART

Electronic/electric components such as light-sensitive sensors (CMOS chips), light emitting diodes (LED) etc. have been increasingly employed in medical devices, for example in endoscopic devices. Especially endoscopes/coloscopes have at the distal end of a flexible endoscope shaft a so called endoscope head in which a number of functional units such as, inter alia, an optical means comprising a lens system and a light-sensitive microchip, a illumination means, preferably a working channel as well as a flushing means, where appropriate, are accommodated. Because of the lack of space existing within the endoscope head the individual functional units are built very closely to each other so that they might have a mutual thermal influence. In other words, especially the illumination means develops thermal energy which must not be discharged exclusively via the outer surface of the endoscope head so as not to damage the adjacent biological tissue (colon, stomach, esophagus etc. of the patient). This thermal energy further results in impairments of the optical means, especially of the usually heat-sensitive light sensor. For this reason, functional units irradiating thermal energy and/or heat-sensitive functional units are in addition actively cooled by means of an integrated cooling device.

From U.S. Pat. No. 7,413,543 B2 a medical endoscope of the relevant species is known. The endoscope head of this known endoscope is formed by a sleeve-like endoscope cap closed at the end face by an integrally formed end plate in which a lens system, an electronic control including a light-sensitive sensor chip, an electric conductor plate having LED positioned thereon as well as a cooling device are incorporated as functional units. Moreover, a working channel which opens to the outside at the end plate is axially passed through the endoscope head.

The cooling device consists of a separate heat exchanger in the form of a semi-cylindrical cooling chamber collar having a fluid inlet and outlet inserted in the endoscope cap. The distal open end face of the separate cooling chamber collar is closed by the electric conductor plate so that cooling fluid directly flows toward the conductor plate inside the chamber and thus cools the LED mounted thereon on the rear side. Simultaneously, the separate cooling chamber collar serves as a support for the lens system. In the end plate through-bores are formed so that the LED can emit light to the outside through the bores after inserting the cooling chamber collar in the endoscope cap. At the proximal closed end face of the cooling chamber collar the electronic control including a light-sensitive sensor chip is arranged so that also the sensor is somewhat cooled by the cooling chamber collar. At the same time, the cooling chamber collar serves as a heat shielding spacer for axially spacing the LED apart from the light-sensitive sensor so as to minimize the mutual thermal influence. In accordance with U.S. Pat. No. 7,413, 543 B2 the cooling chamber collar and the conductor plate including the LED mounted thereon form a separate independent functional unit that is pre-assembled outside the endoscope cap and is then inserted in the cap.

As a result, supports for the cooling chamber collar have to be formed in the endoscope cap. These supports further limit the space available which is quite limited anyway and render the manufacture of the endoscope cap more expensive.

In view of these problems it is the object of the present invention to further develop the endoscope head of a preferably medical endoscope so that it achieves higher efficiency. It is one target to minimize the costs for the manufacture thereof. It is ultimately a target of the invention to obtain more free space by appropriate arrangement and allocation of the individual functional units which free space can be used for additional functional units or enlarged individual functional units.

SUMMARY

The foregoing object is achieved by an endoscope having an endoscope head according to claim 1. Advantageous configurations of the invention are, inter alia, the subject matter of the subclaims.

The fundamental idea of the invention is based on combining as many as possible or especially selected functional units in one integral component so as to save space for supporting and guiding means for the assembly of the individual functional units, wherein the saved space then can be used otherwise, for instance for more voluminous illumination means, a working channel having an enlarged diameter or the like. It is a side effect of this integral design that individual functional units such as the illumination can be moved further toward the distal end face of the endoscope head, where appropriate, so that the efficiency thereof may be improved without the power thereof having to be increased.

Concretely speaking, an endoscope according to an aspect of the invention is consequently provided comprising a flexible endoscope shaft at the distal end of which an endoscope head is arranged consisting of a sleeve (cap) preferably open on both end faces in which sleeve functional units, especially an optical system, a working channel, an illumination and a cooling system for the illumination are accommodated. The cooling system comprises a heat exchanger formed inside the sleeve integrally with the sleeve (preferably by injection molding), the heat exchanger forming a (closed) cooling chamber for generating a coolant flow inside the sleeve (substantially integrally with the sleeve). The illumination in the form of an external conductor plate supporting one or more illumination means is preferably placed in the sleeve so that it is adjacent to the distal end face of the heat exchanger so as to discharge thermal energy through the end wall of the head exchanger into the coolant flow.

The endoscope head sleeve and the heat exchanger or the cooling chamber means, respectively, thus form a single unit adapted to be manufactured in one single manufacturing operation preferably of the same material. This contributes considerably to a reduction of the manufacturing cost. Moreover, further supports, for instance for a separately manufactured cooling chamber means (heat exchanger) as suggested in the prior art can be dispensed with so that also space can be saved. It is further of advantage when the cooling chamber means is directly adjacent to the proximal rear side of the illumination, especially in the form of the conductor plate, so that the illumination, especially in the form of the conductor plate, is adjacent to the outside of the cooling chamber means. In this manner, the transfer of thermal energy into the coolant within the cooling chamber is improved and the efficiency of the cooling system (i.e. of the heat exchanger) is increased. At the same time, the illumination is protected against direct impact by the coolant, because the cooling chamber is internally sealed (cooling chamber means forms a closed cooling chamber) so that the illumination can be provided, for instance, by a conventional LED board that need not exhibit any insulating properties for protection against moisture/wet conditions. This also contributes to reduced costs.

On principle, a board/conductor plate serves for supporting and electrically connecting electric elements such as the illumination means. In accordance with the state of the art, however, such conductor plates can additionally be connected with a (reinforcing) support plate preferably made of aluminum in an electrically insulating manner (by bonding or gluing) so as to obtain higher heat emission while the mechanical strength is increased. In the case of the present invention, it is advantageous to use such (composite) support plate having an increased heat emission capacity so as to improve the transfer of thermal energy through the axial end wall of the heat exchanger/cooling chamber means into the coolant, the (additional) axial end wall internally/integrally sealing the cooling chamber and thus separating the coolant from the conductor plate/composite support plate.

It is advantageous when a radially inwardly projecting support which is integrally supported on the heat exchanger for the working channel and preferably for a flushing channel is formed in the sleeve in the axial area of its distal end face, the support further including an axial through-opening for the optical system. This means that the heat exchanger (first functional unit), the sleeve (second functional unit) for protecting the electric/optical means as well as the supports (third functional unit) for the working and possibly flushing channel are made of a joint component and are mutually stabilizing. In case that this component is an injection molded or pressed part preferably made of plastic material, it can be manufactured in an especially inexpensive manner.

Another, possibly independent aspect of the invention provides that the cooling chamber means forms a coolant path closed toward the outside of the cooling chamber preferably in the form of a channel defined in the cooling chamber which extends along the distal/axial end wall of the heat exchanger/cooling chamber means at least in portions and more preferably forms a number of channel loops so as to increase the distance of the channel. In other words, a further (independent or combinable) aspect of the invention relates to an outwardly fluid-tight, i.e. closed channel system inside the cooling chamber having a coolant inlet and outlet which is passed directly by the distal/axial end wall of the heat exchanger/cooling chamber means at least in portions. I.e. in this case within the cooling chamber sort of a tubular or channel system is formed/used through which coolant is guided in predetermined paths in a manner comparable to a known heat exchanger, wherein the channel walls themselves constitute the afore mentioned end wall or the channel walls are adjacent to the end wall.

Accordingly, the channel system is preferably formed by a (spirally extending) tubing that is separately manufactured and inserted in the cooling chamber or the channel system is formed integrally with the cooling chamber means and thus with the endoscope head sleeve (preferably in one single manufacturing operation).

Another, possibly independent aspect of the invention provides an external (separately manufactured) partition wall which forms the distal/axial end wall of the heat exchanger for sealing and fluid-tight separating the cooling chamber at the end side from the illumination as well as for ensuring transfer of thermal energy from the illumination into the coolant. This has the advantage that the distal/axial end wall of the heat exchanger may exhibit appropriate thermal and mechanical properties such as a heat transfer coefficient increased vis-à-vis the sleeve material. This is especially important when the sleeve rather has a heat insulating effect to protect the patient's surrounding organ tissue. Also, the partition wall may be made of an especially flexible or resilient material which matches the structure at the lower side of the board supporting the illumination means and thus enhances the heat transfer. The partition wall can be provided, for example, in the form of a membrane or film which is glued and/or sealed with the sleeve in a fluid-tight manner.

Another possibly independent aspect of the invention relates to the shape of the distal end wall of the heat exchanger/cooling chamber means in a top view especially when said end wall is formed as a partition wall separately from the sleeve. In this case the partition wall is adapted only to the shape of the cooling chamber, differently/independently from the shape of the external conductor plate supporting the illumination means, so as to axially cover exclusively the cooling chamber means. The conductor plate/board has a plurality of electric elements including electric terminals/contacts which have to be passed by the heat exchanger/cooling chamber. If therefore the partition wall were adapted to the shape of the conductor plate, the partition wall would have to be provided with corresponding through-openings through which the contacts are guided. On principle, the partition wall in that case would be another part of the conductor plate/board.

In accordance with the invention, the partition wall is only adapted to the cooling chamber, i.e. it is part of the heat exchanger and not of the board. In this case, the contacts of the board can also be passed by the partition wall. This spares machining of the partition wall to adapt the same to the board, thereby the manufacturing operation being facilitated.

Furthermore, another possibly independent aspect of the invention provides that the optical system consists of a board supporting a light-sensitive sensor chip on which a lens system is mounted above the chip such that the lens system is held and/or aligned without contacting the sleeve exclusively via the board supporting the sensor chip and is guided freely through the through-opening in the support for the working channel. The support and the sleeve, respectively, thus do not serve for aligning the optical system and therefore can be easily manufactured also with tolerances.

Finally another possibly independent aspect of the invention relates to the distal end face of the sleeve. Consequently, it is provided that the axial portion between the external conductor plate supporting the illumination means and the distal end face of the sleeve is filled with a translucent sealing compound which is either covered, on the front side, by means of a transparent plate or forms the axial end face of the sleeve together with the distal front side of the support for the working channel.

In other words, according to an aspect of the invention the illumination is integrated quasi in the end face of the sleeve. That is to say, the sleeve then does not only serve as protection cap for the incorporated functional units, but is also provided with a corresponding recess at the distal end face thereof or is substantially open at the distal end face so that the illumination can be inserted from the distal side into the sleeve and can be fixed in the latter. This has the advantage that an additional support for the illumination is dispensed with.

Depending on how far the illumination is advanced toward the distal end face of the sleeve, it forms, especially in the case of a board supporting illumination means, part of the distal end plate for axially closing the sleeve, wherein more preferably a translucent plate is put over the printed board so as to protect the electric contacts and conductor paths against moisture, for example. The translucent plate can be put either directly onto the conductor plate (board) supporting the illumination means or onto the end plate. Depending on the wall thickness of the end plate, the translucent plate can also be inserted in the specific through-opening.

BRIEF DESCRIPTION OF THE DRAWINGS

Hereinafter, the invention will be illustrated by way of a preferred embodiment with reference to the accompanying drawing, wherein:

FIG. 1 shows the exploded view of an endoscope head for a flexible medical endoscope according to a preferred embodiment of the invention.

DETAILED DESCRIPTION

In accordance with the enclosed FIG. 1, an endoscope head according to a preferred embodiment of the invention has a cylindrical endoscope head sleeve (hereinafter simply referred to as sleeve) 1 which is adapted to be fixed to the distal end of a preferably flexible endoscope shaft (coloscope shaft) not shown in detail, as it is disclosed, for instance, in the state of the art according to U.S. Pat. No. 7,413,543 B2 mentioned in the beginning.

According to the invention, the sleeve 1 includes a cylindrical sleeve body 1a which at its distal axial end portion or end face has a radially inwardly extending support or a connecting base 2 having substantially pitch circle shape (triangular in top view) inter alia for a working channel, wherein in the present case the support 2 is formed (injection molded) integrally with the sleeve body 1a preferably of a plastic material.

In the support 2 a number of through-bores 4-8 are formed. In particular a central opening 6 is provided to which the working channel not shown in detail is connected and is supported thereon as well as an off-center opening 4 is provided which serves as a through-opening for an optical system, which will be described hereinafter in detail. Moreover, a small-diameter fluid outlet port (flushing port) 8 to which a flushing fluid channel can be connected is formed in the support 2.

As can be inferred from FIG. 1, the distal end face opening of the sleeve 1 is covered only by about a quadrant of the support 2. The remaining portion of the distal end face (thus corresponding to approximately three quarters of a circle) of the sleeve 1 is open, on the other hand. In this context, it is pointed out that ratios of "open" to "closed" may also deviate from said example. If no flushing passage is provided, for example, the support 2 could also be dimensioned to be smaller.

In the open segment of a circle (three quarters of circle in the present case) a heat exchanger is arranged axially behind the distal end face and thus axially stepped back with respect to the support 2, which consists, inter alia, of a cooling chamber means 10 approximately having the shape as shown in FIG. 2 of U.S. Pat. No. 7,413,543, that is, also the cooling chamber means 10 according to the present invention has the outline of a banana or sickle shape (smaller than the open three quarters of a circle) including a central axially extending bulge/cavity/recess having an outline of pitch circle shape, which encompasses the central opening 6 in the support 2. However, in contrast to the state of the art, the cooling chamber means 10 according to the invention is not provided as a component (functional unit) separate from the sleeve 1, but is formed integrally with the sleeve 1, preferably in one single manufacturing step (injection molding method) as well as of the same material as the sleeve 1. By reason of this integral configuration the support 2 as well as the heat exchanger form a joint component part together with the sleeve 1, the support 2 being supported along its entire periphery on the heat exchanger (on the wall of the cooling chamber means 10) in a sealing manner.

A first electronic part 12 is provided axially behind the cooling chamber means 10 and behind the heat exchanger, respectively, in the form of a conductor plate or board in the present case on which a number of electronic components such as, inter alia, a light-sensitive sensor (e.g. CMOS chip) 13 and a storage unit or an interface for electric data transmission, where appropriate, is provided. Furthermore, a lens system 14 is placed and aligned above the light-sensitive sensor 13 on the board 12. The board 12 is provided with engaging means (not shown in detail) by means of which the board 12 is adapted to be fixed in the sleeve body 1a. Especially the sleeve body 1a exhibits in its proximal end portion correspondingly formed locking members arranged so that after being locked in the sleeve body 1a the board 12 constitutes the proximal terminal/closure thereof at the end face opposite to the distal end face of the sleeve 1. Finally, on the first board 12 a number of electric terminals are arranged by which the board 12 can be connected, inter alia, to electric wires in the endoscope shaft not shown.

The light-sensitive sensor 13 and the lens system 14 fixed there above are placed on the first board 12 so that in the mounted state of the first printed board 12 they are arranged behind the off-center opening 4 in the support 2. The axial length of the cooling chamber 10 is moreover dimensioned depending on the construction height of the lens system 14 so that the lens system 14 is directly connected to the off-center opening 4 or even projects axially forward through the same. The off-center opening 4 has a diameter which is larger than the outer diameter of the lens system 14 so that the lens system 14 does not contact the rim of the opening. The off-center opening 4 is preferably sealed by a translucent pane 16 (made of PLEXIGLAS®, glass, acrylic glass etc.) to protect the lens system 14 against contamination.

Furthermore, an illumination is provided in the form of a second conductor plate or board 18 on which a number of illumination means, for instance LED or glow lamps 20, are mounted and electrically interconnected. The second conductor plate 18 in addition has electric terminals for a power supply of the illumination means 20 which are adapted to be brought in electric contact with terminals on the first board 12. The second conductor plate 18 moreover has an outline corresponding to three quarters of a circle and thus to the rim contour of the support 2 inside the sleeve 1 (which is thus larger in this case than the end face of the cooling chamber 10) such that the second conductor plate 18 can be inserted in the sleeve 1 (in the three quarters of a circle) from the distal end face. Finally also the second conductor plate 18 can be covered by means of transparent filler and/or a translucent pane 22 of said material which is fixed to the end face of the sleeve 2 or directly to the second conductor plate 18.

Inside the cooling chamber of the cooling chamber means 10 a coolant flow path 11 is formed which is separated from or closed in a fluid-tight manner against the second conductor plate 18 so that no coolant can directly reach/contact the second conductor plate 18. The flow path is connected to a supply and discharge tube in the endoscope shaft not shown via inlets and outlets in the cooling chamber 10. The fluid-tight separation of the cooling chamber means/the flow path 11 and the second conductor plate 18 can be performed by different constructional measures:

In accordance with a variant, it is provided to insert/glue/cast a partition wall 24 between the second conductor plate 18 and the cooling chamber in the sleeve 1, the peripheral shape of the partition wall corresponding to the shape of the cooling chamber (i.e. being smaller than the second board 18) so that the partition wall 24 covers exclusively the cooling chamber of the cooling chamber means 10. As one can infer from FIG. 1, also at the second conductor plate 18 a number of electric contacts or terminals are arranged which are passed by the heat exchanger (by the cooling chamber means 10) so as to contact corresponding contacts at the first conductor plate 12. Since the partition wall 24 is shaped so that it covers only the cooling chamber of the cooling chamber means 10 in a sealing manner, consequently it is a closing plate of the cooling chamber having a thickness of approximately 0.3 mm, it need not be provided with recesses or through-bores for the terminals of the second conductor plate 18, for instance.

The partition wall 24 preferably consists of a (flexible) membrane or film. Such film or membrane is fixed to the open end face of the cooling chamber in a sealing manner so that it maintains mechanical, but at least thermal contact with the second conductor plate 18 inserted afterwards. The partition wall 24 can be made of the same material as the sleeve 1 (i.e. in general a plastic material), but it can also consist of a coated tissue or a metallic/aluminum film. Also other materials adapted to be connected to the sleeve material in a fluid-tight manner and having a still sufficient heat transfer coefficient are possible.

According to a preferred variant of the invention (as also illustrated in FIG. 1), it is provided to arrange/form a channel system inside the cooling chamber of the cooling chamber means 10 having a closed channel/tubular wall 11 through which coolant is passed. This channel system according to the principle of a known heat exchanger includes a preferably looped longitudinal portion for an expanded distance which longitudinal portion is guided directly along the partition wall 24 and consequently is in thermal contact with the second conductor plate 18 via the partition wall 24. In this case, the partition wall 24 serves for axially sealing/closing the channel system 11.

Finally, it is also possible to design the channel system 11 according to FIG. 1 by an external tube being inserted in the cooling chamber and connected to the inlet and outlet of the heat exchanger. In this case, too, a partition wall 24 according to FIG. 1 can be additionally provided.

It is necessary for the second conductor plate 18 that thermal energy generated by the illumination means 20 is discharged to the coolant with high efficiency. For this purpose, the invention preferably makes use of boards according to the IMS (insulated metallic substrate) technology consisting of an electrically conducting layer for the manufacture of conductor paths, an electrically insulating intermediate layer and a carrier layer/substrate preferably of an aluminum plate which are glued together to form a composite conductor plate. Basically it is also possible to use a conventional board also known as FR4 board among experts.

The assembly of the endoscope head according to the invention can be described as follows:

Initially all supply channels such as flushing channel, working channel etc. are formed already in the sleeve 1 and are integrally coupled with the corresponding ports 6, 8 in the support base 2. Accordingly, firstly the partition wall 24 is inserted from the axial distal outside of the sleeve 1 into the substantially three quarter circle opening of the sleeve 1 and is glued/sealed custom-fit to/in the axial end face of the cooling chamber so that a heat exchanger/cooling chamber means 10 closed in itself in a fluid-tight manner is formed hereby.

As already described in the foregoing, the partition wall 24 is adapted substantially, preferably exactly, to the contour of the cooling chamber means 10 so that only the latter is covered in a sealing manner by the partition wall 24 and therefore axial passageways inside the sleeve 1 are kept free for electric contacts or cables.

After that, the second board (as pre-assembled unit) 18 is inserted equally from the axial distal outside of the sleeve 1 into the preferably three quarter circle opening of the sleeve 1 and is then fixed in the sleeve 1 (glued and/or clamped). Preferably the second board 18 is partly supported with its back side on the partition wall 24 in the portion of the board which overlaps with the partition wall 24.

Ultimately the translucent sealing compound gets into the three quarter circle opening and, optionally, the cover pane 22 is put above the second board 18 as well as the pane 16 is put above the opening 4 each of which is glued in/on the sleeve 1 in a fluid-tight manner. At this assembling position the second board or conductor plate 18 is adjacent with its rear side to the partition wall 24 which closes the interior of the cooling chamber 10 toward the second conductor plate 18 in a fluid-tight manner. In addition, between the second conductor plate 18 and the partition wall (membrane/film) 24 preferably sticky filler can be disposed for even improving the heat transfer between the second conductor plate 18 and the partition wall 24. The electric contacts of the second conductor plate 18 are passed by the cooling chamber and the partition wall 24 and axially project proximally from the cooling chamber.

Finally, the first conductor plate (as pre-assembled unit) 12 is inserted in the sleeve body 1a from the proximal end face, the electric contacts toward the second conductor plate 18 preferably closing automatically. The first conductor plate 12 is necessarily aligned upon insertion due to the present locking means so that the optical system comprising the light-sensitive sensor 13 and the lens system 14 is arranged exactly below the corresponding off-center opening 4 in the support 2, wherein the optical system is likewise aligned exclusively by the first conductor plate 12 and the correct assembly position thereof. The optical system itself has no direct contact with the sleeve 1. Upon locking of the first board 12 in the sleeve 1 the lens system 14 advances through the corresponding off-center opening 4 so that an unobstructed view to the front and possibly radially to the side of the sleeve 1 is permitted.

Concluding, the present invention will be summarized once again as follows:

An endoscope comprising a flexible endoscope shaft is disclosed at the distal end of which an endoscope head is arranged consisting of a sleeve open at both end faces in which functional units, especially an optical system, a working channel, an illumination and a cooling system for the illumination are accommodated. In accordance with the invention, the cooling system comprises a heat exchanger integrally formed with the sleeve in the latter which forms a closed cooling chamber for generating a coolant flow. The illumination in the form of an external conductor plate supporting illumination means is placed so that it is adjacent to (is mechanically supported on or has only a minimum distance from) the distal end wall of the heat exchanger in order to discharge thermal energy via the end wall of the heat exchanger into the coolant flow.

What is claimed is:

1. An endoscope, comprising:
   a flexible endoscope shaft;
   an endoscope head, arranged at a distal end of the endoscope shaft, comprising:
      a sleeve, open at, at least, one end face thereof;
      functional units accommodated in the sleeve, the functional units comprising an optical system, a working channel, an illumination and a cooling means at least for the illumination, the cooling means comprising a heat exchanger unitarily formed in the sleeve with a cooling chamber formed together with the sleeve for generating a coolant flow;
      a support, projecting radially inwardly and integrally supported on the heat exchanger, for a working channel, the support being formed in the sleeve in the axial area of its distal end face and comprising an axial through-opening for the optical system;
   wherein the cooling chamber forms a coolant path closed to the outside of the cooling chamber in the form of a channel defined in the cooling chamber which extends at least in portions along a distal end wall of the heat exchanger and forms a number of channel loops preferably for increasing the channel distance; and
   wherein the optical system comprises a conductor plate supporting a light-sensitive sensor chip on which a lens system is mounted above the sensor chip at the sensor chip and/or at the conductor plate such that the lens system is held and/or aligned without contacting the sleeve exclusively via the conductor plate supporting the sensor chip and is guided freely through the axial through-opening for the optical system in the support for the working channel.

2. The endoscope of claim 1, wherein:
   the illumination, in the form of an external conductor plate that supports an illumination means, is adjacent to the distal end wall of the heat exchanger, the distal end wall closing the cooling chamber in a fluid-tight manner so as to discharge thermal energy via the distal end wall of the heat exchanger to the coolant flow.

3. The endoscope of claim 2, further comprising:
   an external separate partition wall which forms the distal end wall of the heat exchanger for sealing at the end face and separating the cooling chamber in a fluid-tight manner from the external conductor plate supporting illumination means as well as for ensuring transfer of thermal energy from the illumination means to the coolant.

4. The endoscope of claim 3, wherein:
   the partition wall is adapted, differently from or independently of the shape of the external conductor plate supporting the illumination means, to the shape of the cooling chamber so as to axially cover exclusively the cooling chamber.

5. The endoscope of claim 2, wherein:
   the distal end wall of the heat exchanger is a membrane or film that is glued and/or sealed with the sleeve in a fluid-tight manner.

6. The endoscope of claim 2, wherein:
   an axial portion of the sleeve between the external conductor plate supporting illumination means and the distal end face of the sleeve is filled with a translucent sealing compound which is covered at the end face either by a transparent plate or which forms the axial end face of the sleeve together with a distal front side of the support for the working channel.

7. The endoscope of claim 2, wherein:
   the sleeve and the heat exchanger including the cooling chamber are in the form of a single unitary injection molded part made of plastic material preferably with the exception of the distal end wall closing the cooling chamber.

8. The endoscope of claim 1, wherein:
   the channel is formed by a tubing which is manufactured separately and is inserted in the cooling chamber or which is formed integrally with the cooling chamber and thus with the sleeve.

9. The endoscope of claim 1, further comprising:
   a coolant inlet and outlet formed at angular distance from each other at the proximal end face of the heat exchanger.

10. The endoscope of claim 1, wherein:
    the conductor plate supporting the sensor chip is mounted transversely to the axial direction of the sleeve and constitutes the proximal end of the sleeve at the end face.

11. The endoscope of claim 10, wherein:
    the heat exchanger has an axial length adapted to the optical system in such way that the lens system when mounted above the sensor chip ends in the through-opening of the support or projects axially from the through-opening in the distal direction.

12. The endoscope of claim 10, wherein:
    the conductor plate is mounted in parallel to the distal end face of the sleeve.

13. The endoscope of claim 1, wherein:
    the sleeve and the heat exchanger including the cooling chamber are in the form of a single unitary injection molded part made of plastic material.

14. The endoscope of claim 1, further comprising:
    a flushing channel, supported by the radially inwardly projecting support.

* * * * *